United States Patent
Pei et al.

(10) Patent No.: US 6,593,687 B1
(45) Date of Patent: Jul. 15, 2003

(54) CAVITY-EMISSION ELECTROLUMINESCENT DEVICE AND METHOD FOR FORMING THE DEVICE

(75) Inventors: Qibing Pei, Fremont, CA (US); Seajin Oh, Palo Alto, CA (US)

(73) Assignee: SRI International, Menlo Park, CA (US)

(*) Notice: Subject to any disclaimer, the term of this patent is extended or adjusted under 35 U.S.C. 154(b) by 538 days.

(21) Appl. No.: 09/618,864

(22) Filed: Jul. 19, 2000

Related U.S. Application Data
(60) Provisional application No. 60/144,938, filed on Jul. 20, 1999.

(51) Int. Cl.[7] .............................................. H05B 33/10
(52) U.S. Cl. ...................... 313/504; 313/505; 313/509; 445/24
(58) Field of Search ........................... 445/24; 313/503, 313/505, 506, 509, 504

(56) References Cited

U.S. PATENT DOCUMENTS

| | | | |
|---|---|---|---|
| 4,539,507 A | | 9/1985 | VanSlyke et al. |
| 4,614,668 A | * | 9/1986 | Topp et al. ............... 313/505 |
| 5,086,297 A | * | 2/1992 | Miyake et al. ............ 313/485 |
| 5,247,190 A | | 9/1993 | Friend et al. |
| 5,442,256 A | * | 8/1995 | Moyer et al. ............. 313/496 |
| 5,677,546 A | | 10/1997 | Yu |
| 5,682,043 A | | 10/1997 | Pei et al. |
| 5,723,873 A | | 3/1998 | Yang |
| 5,807,627 A | | 9/1998 | Friend et al. |
| 5,869,350 A | | 2/1999 | Heeger et al. |
| 5,895,717 A | | 4/1999 | Cao et al. |
| 5,900,327 A | | 5/1999 | Pei et al. |
| 5,962,631 A | | 10/1999 | Woo et al. |
| 5,966,393 A | | 10/1999 | Hide et al. |
| 6,091,195 A | | 7/2000 | Forrest et al. ........... 313/504 |

FOREIGN PATENT DOCUMENTS

| | | |
|---|---|---|
| EP | 0776052 | 5/1997 |
| EP | 0878883 | 11/1998 |
| EP | 0886329 | 12/1998 |
| EP | 0892028 | 1/1999 |
| EP | 0892590 | 1/1999 |
| WO | WO98/10473 | 3/1998 |
| WO | WO 98/27136 | 6/1998 |
| WO | WO98/31057 | 7/1998 |

OTHER PUBLICATIONS

Baigent et al. (1994), "Conjugated Polymer Light–Emitting Diodes on Silicon Substrates," *Appl. Phys. Lett.* 65 (21):2636–2638.

Rost et al. (1996), "Novel Light Emitting and Photoconducting Polyarylenevinylene Derivatives Containing Phenylene Arylamine and Phenylene Oxide Units in the Main Chain," *International Conference on Synthetic Metals*, Utah.

Smela et al. (1998), "Planar Microfabricated Polymer Light–Emitting Diodes," *Semicond. Sci. Technol.* 13:433 439.

Rost et al. (1997), "Novel Light Emitting and Photoconducting Polyarylenevinylene Derivatives Containing Phenylene Arylamine and Phenylene Oxide Units in the Main Chain," *Synthetic Metals* 84: 269–270.

* cited by examiner

*Primary Examiner*—Kenneth J. Ramsey
(74) *Attorney, Agent, or Firm*—Reed & Eberle LLP; Louis L. Wu

(57) ABSTRACT

An electroluminescent device and a method for producing the electroluminescent device are described. The device is formed from a layered structure comprising a hole-injection electrode layer for injecting holes into an electroluminescent material, an electron-injection electrode layer for injecting electrons into an electroluminescent material and a dielectric layer interposed between the hole-injecting and electron-injecting electrode layers. A cavity extends through at least the dielectric layer and one of the electrode layers and has an interior cavity surface comprising a hole-injection electrode region, an electron-injection electrode region and a dielectric region. An electroluminescent coating material is applied to the interior cavity surface in order to electrically contact the hole-injection and electron-injection electrode regions of the interior cavity surface.

45 Claims, 7 Drawing Sheets

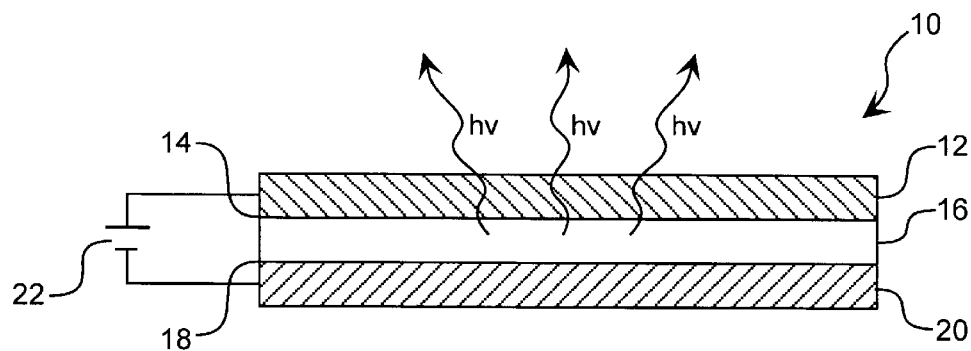
FIG. 1 - PRIOR ART
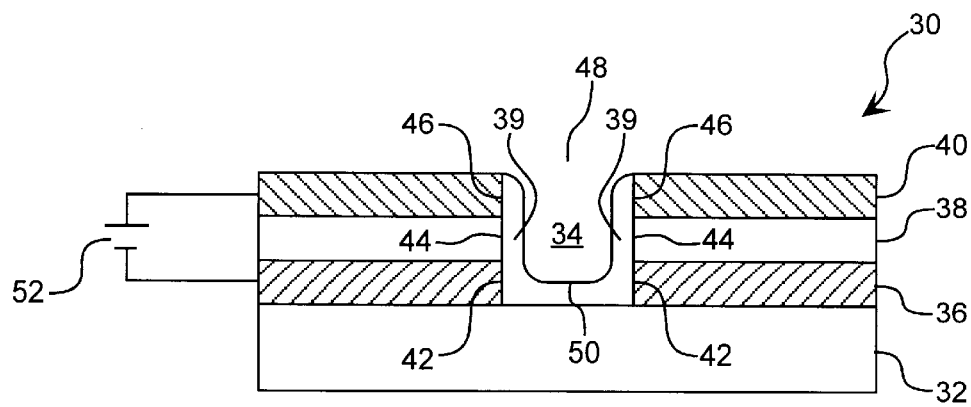
FIG. 2

US 6,593,687 B1

CAVITY-EMISSION ELECTROLUMINESCENT DEVICE AND METHOD FOR FORMING THE DEVICE

CROSS-REFERENCE TO RELATED APPLICATIONS

This application claims priority to U.S. Provisional Patent Application Serial No. 60/144,938, filed Jul. 20, 1999.

TECHNICAL FIELD

This invention relates generally to the field of light-emitting displays. More particularly, the invention relates to a novel cavity-emission electroluminescent device and a method for forming such a device.

BACKGROUND

Electroluminescent devices have become increasingly important within the display industry. Such devices are usually constructed in a multilayer thin-film or "sandwich" configuration comprising a layer of electroluminescent material interposed between electron-injection and hole-injection electrode layers. When a voltage is applied to the electrode layers, holes and electrons are injected into the electroluminescent material from the hole injection and electron-injection electrode layers, respectively. Once the holes and electrons are combined in the electroluminescent material, light is emitted through one of the electrode layers. These electroluminescent devices have been described, e.g., in U.S. Pat. No. 5,247,190 to Friend et al., U.S. Pat. No. 5,682,043 to Pei et al., U.S. Pat. No. 5,723,873 to Yang and in Baigent et al. (1994), "Conjugated Polymer Light-Emitting Diodes on Silicon Substrates," *Appl. Phys. Letter*, 65(21):2636–38.

In the past, electroluminescent devices have used relatively small organic molecules as the electroluminescent material. See e.g., U.S. Pat. No. 4,539,507 to Van Slyke et al. However, much interest has recently been shown in the use of conjugated polymers in electroluminescent devices. For example, there is a present need for flexible displays. In order to produce a flexible electroluminescent device using an ordinary multilayer thin film configuration, each layer must have mechanical properties that can withstand the stresses and strains associated with deformation due to flexing. Thus, polymeric electroluminescent materials are preferred over relatively simple electroluminescent molecules. Electroluminescent polymers have been described in detail in a number of patents and publications such as U.S. Pat. No. 5,962,631 to Woo et al., International Patent Publication No. WO 98/27136 and Horhold et al., (1997), "Novel Light Emitting and Photoconducting Polyarylene Vinylene Derivatives Containing Phenylene Arylamine and Phenylene Oxide Units in the Main Chain," *Synthetic Metals*, 84:269–70.

Ordinarily, the display configuration as described above requires at least one of the electrodes to be transparent with respect to the emitted light. See, e.g., U.S. Pat. No. 5,869,350 to Heeger et al. This is problematic because there are very few transparent materials that exhibit sufficient electrical conductivity to serve as an electrode material. Indium tin oxide (ITO) is one such optically transparent electrode material. However, the conductivity of ITO is more than an order of magnitude lower than that of most metals and is thus not an optimal material for display applications requiring a fast electroluminescent response. In addition, ITO lacks chemical stability for certain electroluminescent display applications. Moreover, because ITO is only a semi-transparent material, ITO represents a source of internal device reflection when used as an electrode material in a multilayer configuration as described above.

In addition, multicolored displays using the above-described configuration are relatively difficult and expensive to produce due to inherent materials and processing limitations. In such a configuration, the electroluminescent layer serves to ensure that the electrode layers are electrically insulated from each other. Thus, the electroluminescent layer must be pinhole free. In addition, given the electronic properties of typical electroluminescent materials, the electroluminescent layer must have a uniform thickness of about 1000 to 2000 angstroms. This uniformity requirement is problematic because there is no known technique that can reliably and inexpensively produce color pixels in a uniform manner over a large area electroluminescent layer. While it may be possible to photolithographically pattern colors on electroluminescent polymers via photoresists, photoresist processing may adversely affect the uniformity in the thickness of the electroluminescent layer. Moreover, electroluminescent emission by the pixels in a direction parallel to the layers reduces the contrast between pixels. In turn, display resolution is compromised.

Some have proposed device configurations other than the above described layered or "sandwich" structure. For example, U.S. Pat. No. 5,677,546 to Yu describes another configuration in which a light-emitting electrochemical cell may be made. Comprising an anode, a cathode and an electroluminescent film, the cell is constructed in a surface cell configuration, i.e., the anode and the cathode are in electrical contact with the same side of the electroluminescent film. The patent states that the electrodes may be formed using masking techniques such as photolithography. As another example, Smela et al., (1998), "Planar microfabricated Polymer Light-Emitting Diodes," *Semicond. Sci. Technol.*, 13:433–39 describes an alternative device configuration. This article reports that diodes having interdigitated electrodes may be capable of electroluminescence even if the electrodes are separated by a distance of tens of microns. However, both these device configurations suffer from low brightness as the actual light emission zone is only a small fraction of the device area.

There is accordingly a need in the art to for an electroluminescent device that is capable of overcoming the inherent limitation of prior device configurations to provide a lightweight, high-efficiency and bright display device.

SUMMARY OF THE INVENTION

The present invention is addressed to the aforementioned need in the art, and provides a novel, low-cost, lightweight and easily fabricated cavity-emission electroluminescent device.

It is another object of the invention to provide such a display device that exhibits superior contrast, resolution and high power efficiency.

It is still another object of the invention to provide such a device that is suitable for a multicolor display.

It is a further object of the invention to provide a method for forming such a device.

Additional objects, advantages and novel features of the invention will be set forth in part in the description which follows, and in part will become apparent to those skilled in the art upon examination of the following, or may be learned by practice of the invention.

In one embodiment, then, the invention relates to an electroluminescent device. The device is comprised of a layered structure having a hole-injection electrode layer for injecting holes into an electroluminescent material, an electron-injection electrode layer for injecting electrons into an electroluminescent material and a dielectric layer interposed between the hole-injecting and electron-injecting electrode layers. A cavity extends through at least the dielectric layer and one of the electrode layers and has an interior cavity surface comprising a hole-injection electrode region, an electron-injection electrode region and a dielectric region. An electroluminescent coating material is provided in electrical contact with the hole-injection and electron-injection electrode regions of the interior cavity surface.

In another embodiment, the invention relates to a method for forming an electroluminescent device. The method involves providing a layered structure as described above having a cavity with an interior surface comprising a hole-injection electrode region, an electron-injection electrode region and a dielectric region. In one aspect, an etchant may be used to etch through a portion of a preformed layered structure to form the cavity. In another aspect, the layered structure may be formed around a sacrificial member having a desired size and shape for the cavity, wherein the sacrificial member is later removed to expose the interior cavity surface. Once the cavity is formed, the interior cavity surface is coated with an electroluminescent coating material such that the electroluminescent material electrically contacts the hole-injection and electron-injection electrode regions of the surface.

In a further embodiment, the invention relates to an electroluminescent display device. The display device comprises a layered structure as described above containing a plurality of cavities each extending through at least two layers of the layered structure such that each cavity has an interior cavity surface comprising a hole-injection electrode region, an electron-injection electrode region and a dielectric region. An electroluminescent material is provided in electrical contact with the hole-injection and electron-injection electrode regions of each interior cavity surface. Preferably, the plurality of cavities is arranged in an array.

BRIEF DESCRIPTION OF THE DRAWING

FIG. 1 schematically illustrates in simplified cross-sectional view a prior art electroluminescent device having a multilayered thin film configuration, in which an electroluminescent layer is interposed between two electrode layers and one electrode layer is transparent to the wavelength of electromagnetic radiation emitted by the electroluminescent layer.

FIG. 2 schematically illustrates in simplified cross-sectional view an electroluminescent device of the invention comprising a layered structure on a substrate and a cavity extending through the layered structure. The cavity has an interior surface comprising a hole-injection electrode region, a dielectric region and an electron-injection electrode region. An electroluminescent material coating is shown in conformal and electrical contact with the electrode regions of the interior cavity surface.

FIGS. 5A, 5B and 5C illustrate the formation of a layered structure on a substrate wherein the layered structure comprises a hole-injection electrode layer, a dielectric layer, and electron-injection electrode layer. FIGS. 5D and 5E, 5F and 5G illustrate the formation of a cavity through the layered structure by using a lithographic and etching technique. FIGS. 5H and 5I illustrate the application of an electroluminescent coating material to the interior surface of the cavity such to achieve conformal contact between the coating material and the interior surface.

FIGS. 6A and 6B illustrate the formation of a sacrificial member in the shape of a desired cavity for the layered structure. FIGS. 6C and 6D illustrate the formation of a layered structure on a substrate around the sacrificial member, wherein the layered structure comprises a hole-injection electrode layer, a dielectric layer, and electron-injection electrode layer. FIGS. 6E illustrates the removal of the sacrificial member to expose the interior surface of the cavity of the layered structure.

DETAILED DESCRIPTION OF THE INVENTION

Definitions and Overview

Figure 3:
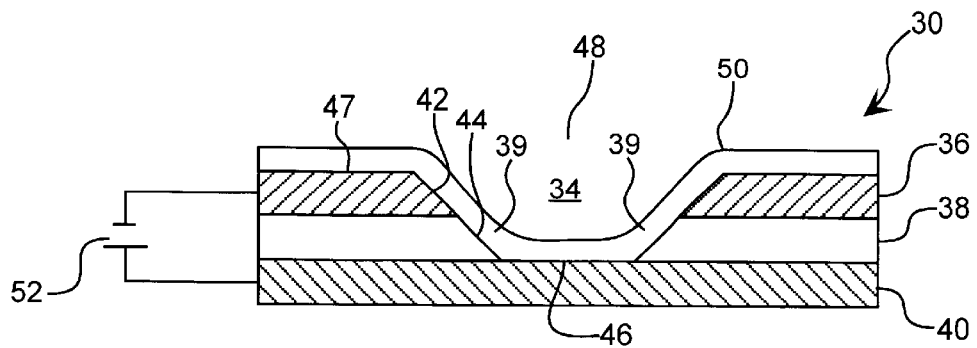
FIG. 3 schematically illustrates in simplified cross-sectional view another electroluminescent device of the invention comprising a layered structure wherein one electrode layer serves as a device substrate. A cavity is shown extending only partially through the layered structure, terminating at the substrate and filled with an electroluminescent material.

Before the invention is described in detail, it is to be understood that unless otherwise indicated this invention is not limited to particular materials, components or manufacturing processes, as such may vary. It is also to be understood that the terminology used herein is for purposes of describing particular embodiments only, and is not intended to be limiting. It must be noted that, as used in the specification and the appended claims, the singular forms "a," "an" and "the" include plural referents unless the context clearly dictates otherwise. Thus, for example, reference to reference to "an electrode layer" encompasses more than one electrode layer, "a polymer" includes mixtures of different polymers, and the like.

The term "array" used herein refers to a regular, orderly, and two-dimensional pattern of features such as cavities. Arrays typically but do not necessarily comprise at least about 100 and preferably at least about 1000 cavities.

The term "dielectric strength" is used herein to refer the ability of an electrically insulating material to withstand exposure to an electric field without electrical breakdown, i.e., loss of mechanical integrity. Dielectric strength is sometimes described as having two components, electronic and thermal. Electronic breakdown is caused by the excessive liberation of electrons and usually dominates the electrical breakdown process at a low temperature. Thermal breakdown, on the other hand, is caused by the localized heating due to material heterogeneities and dominates the electrical breakdown process at a higher temperature. Typically, dielectric strength is calculated in terms of volts per centimeter.

The term "electroluminescent" is used herein to describe a material or a device that emits electromagnetic radiation, preferably in the visible range, upon application of an electrical potential and/or current. When electrons and holes are injected into an electroluminescent material, light is emitted upon the combination of the electrons and holes, thereby resulting in electroluminescence.

The term "etchant" is used in its ordinary sense and refers to matter that is capable of chemically removing material from a solid body. An "isotropic etchant" is an etchant that removes material from a solid surface in a direction-invariant manner, whereas an "anisotropic etchant" preferentially removes material from a solid surface in a particular direction, e.g., according to crystallographic orientation of the solid body or the direction of the light energy particles for light assisted etching.

The term "electrical contact" is used herein to refer to a connection between two bodies that permits a flow of current, i.e., transfer of electrons or holes from one body to the other, which usually but does not necessarily imply direct mechanical contact between the two bodies.

The term "emission modifier" refers to a compound that alters the emission spectrum of an electroluminescent material. The emission modifier may be itself an electroluminescent or luminescent material.

"Optional" or "optionally" means that the subsequently described event or circumstance may or may not occur, and that the description includes instances where said event or circumstance occurs and instances where it does not. For example, an electroluminescent device comprising an "optional substrate" means that the substrate may or may not be present and that the description includes either state.

The term "substrate" is used herein in its ordinary sense and means a body or base layer onto which other layers are deposited. Usually, a substrate is used to provide the layered structure of the invention sufficient mechanical strength for handling.

In describing molecular structures, e.g., of arylamine-substituted poly(arylene vinylenes) useful in conjunction with the invention, the following definitions apply:

The term "alkyl" as used herein refers to a branched or unbranched saturated hydrocarbon group typically although not necessarily containing 1 to about 24 carbon atoms, such as methyl, ethyl, n-propyl, isopropyl, n-butyl, isobutyl, t-butyl, octyl, 2-ethylhexyl, decyl, and the like, as well as cycloalkyl groups such as cyclopentyl, cyclohexyl and the like. Generally, although again not necessarily, alkyl groups herein contain 1 to about 12 carbon atoms. The term "lower alkyl" intends an alkyl group of one to six carbon atoms, preferably one to four carbon atoms. "Substituted alkyl" refers to alkyl substituted with one or more substituent groups, and the terms "heteroatom-containing alkyl" and "heteroalkyl" refer to alkyl in which at least one carbon atom is replaced with a heteroatom.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing one to six, more preferably one to four, carbon atoms.

The term "aryl" as used herein, and unless otherwise specified, refers to a univalent aromatic substituent containing a single aromatic ring or multiple aromatic rings that are fused together or linked covalently. Preferred aryl groups contain one aromatic ring or two fused or linked aromatic rings, e.g., phenyl, naphthyl, biphenyl, fluorenyl, and the like. "Substituted aryl" refers to an aryl moiety substituted with one or more substituent groups, and the terms "heteroatom-containing aryl" and "heteroaryl" refer to aryl in which at least one carbon atom is replaced with a heteroatom.

The term "arylene" as used herein, and unless otherwise specified, refers to a divalent aromatic substituent containing a single aromatic ring or multiple aromatic rings that are fused together or linked covalently. Preferred arylene groups contain one aromatic ring or two fused or linked aromatic rings. "Substituted arylene" refers to an arylene moiety substituted with one or more substituent groups, and the terms "heteroatom-containing arylene" and "heteroarylene" refer to arylene in which at least one carbon atom is replaced with a heteroatom.

The term "aralkyl" refers to an alkyl group with an aryl substituent, and the term "aralkylene" refers to an alkylene group with an aryl substituent; the term- "alkaryl" refers to an aryl group that has an alkyl substituent, and the term "alkarylene" refers to an arylene group with an alkyl substituent.

The terms "halo" and "halogen" are used in the conventional sense to refer to a chloro, bromo, fluoro or iodo substituent. The terms "haloalkyl," "haloalkenyl" or "haloalkynyl" (or "halogenated alkyl," "halogenated alkenyl," "halogenated aromatic" or "halogenated alkynyl") refers to an alkyl, alkenyl, aromatic or alkynyl group, respectively, in which at least one of the hydrogen atoms in the group has been replaced with a halogen atom.

The term "heteroatom-containing" refers to a molecule or molecular fragment in which one or more carbon atoms is replaced with an atom other than carbon, e.g., nitrogen, oxygen, sulfur, phosphorus or silicon. Similarly, the term "heteroalkyl" refers to an alkyl substituent that is heteroatom-containing, the term "heterocyclic" refers to a cyclic substituent that is heteroatom-containing, the term "heteroaryl" refers to an aryl substituent that is heteroatom-containing, and the like.

"Hydrocarbyl" refers to univalent hydrocarbyl radicals containing 1 to about 30 carbon atoms, preferably 1 to about 24 carbon atoms, most preferably 1 to about 12 carbon atoms, including branched or unbranched, saturated or unsaturated species, such as alkyl groups, alkenyl groups, aryl groups, and the like. The term "lower hydrocarbyl" intends a hydrocarbyl group of one to six carbon atoms, preferably one to four carbon atoms. The term "hydrocarbylene" intends a divalent hydrocarbyl moiety containing 1 to about 30 carbon atoms, preferably 1 to about 24 carbon atoms, most preferably 1 to about 12 carbon atoms, including branched or unbranched, saturated or unsaturated species, or the like. The term "lower hydrocarbylene" intends a hydrocarbylene group of one to six carbon atoms, preferably one to four carbon atoms. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom. Similarly, "substituted hydrocarbylene" refers to hydrocarbylene substituted with one or more substituent groups, and the terms "heteroatom-containing hydrocarbylene" and "heterohydrocarbylene" refer to hydrocarbylene in which at least one carbon atom is replaced with a heteroatom.

A "Lewis acid" refers to any species with a vacant orbital, in contrast to a "Lewis base," which refers to a compound with an available pair of electrons, either unshared or in a π-orbital. Typically, a Lewis acid refers to a compound containing an element that is two electrons short of having a complete valence shell.

By "substituted" as in "substituted hydrocarbyl," "substituted hydrocarbylene," "substituted alkyl," "substituted alkenyl" and the like, as alluded to in some of the aforementioned definitions, is meant that in the hydrocarbyl, hydrocarbylene, alkyl, alkenyl or other moiety, at least one hydrogen atom bound to a carbon atom is replaced with one or more substituents that are functional groups such as hydroxyl, alkoxy, thio, amino, halo, silyl, and the like. When the term "substituted" appears prior to a list of possible substituted groups, it is intended that the term apply to every member of that group. That is, the phrase "substituted alkyl, alkenyl and alkynyl" is to be interpreted as "substituted alkyl, substituted alkenyl and substituted alkynyl." Similarly, "optionally substituted alkyl, alkenyl and alkynyl" is to be interpreted as "optionally substituted alkyl, optionally substituted alkenyl and optionally substituted alkynyl."

In one embodiment, then, the invention provides an electroluminescent composed of a layered structure comprising a hole-injection electrode layer, an electron-injection electrode layer and a dielectric layer interposed between the hole-injecting and electron-injecting electrode layers. A cavity extends through at least the dielectric layer and one of the electrode layers and has an interior cavity surface comprising a hole-injection electrode region, an electron-injection electrode region and a dielectric region. An electroluminescent coating material is provided in electrical contact with the hole-injection and electron-injection electrode regions of the interior cavity surface. As result, the device is configured for edge emission, i.e., for emitting light near a cavity surface between the edges of two electrodes rather than through an electrode. Such a configuration provides manufacturing advantages and improved performance in thin film display application. Moreover, this configuration allows for the manufacturing of flexible displays.

To provide an example of a prior art device and to illustrate the disadvantages associated therewith, FIG. 1 schematically illustrates in a simplified cross-sectional view a prior art electroluminescent device having a multilayered thin film configuration. As with all figures referenced herein, in which like parts are referenced by like numerals, FIG. 1 is not to scale, and certain dimensions may be exaggerated for clarity of presentation. The prior art electroluminescent device 10 is in a multilayer thin film configuration having electron-injection and hole-injection electrode layers indicated at 12 and 20, respectively. Interposed between the electrode layers is an electroluminescent layer 16. The electroluminescent layer is in contact with each electrode layer. As a result, an electron-injection interface 14 is formed between the electron-injection electrode layer 12 and the electroluminescent layer 16, and a hole-injection interface 18 is formed between the electroluminescent layer 16 and the hole-injection electrode layer 20.

In operation, each electrode is connected to a power supply 22. The power supply 22 produces a voltage difference between the electrode layers. As a result, electrons are injected from the electron-injection electrode layer 12 across the electron-injection interface 14 into the electroluminescent layer 16, and holes are injected from the hole-injection electrode layer 20 across the hole-injection interface 18 into the electroluminescent layer 16. It should be evident that each of the electrode layers must be composed of a material having sufficient electrical conductivity in order to operate as an electrode. When the electrons and the holes combine, visible electromagnetic radiation is emitted and transmitted through one of the electrodes, as indicated by the arrows marked "hv."

This configuration suffers from a variety of drawbacks. First, at least one of the electrodes must be transparent to the emitted electromagnetic radiation in order for this device to operate as a light-emitting device. Currently, there are very few known electrically conductive materials that have sufficient transparency and electrical conductivity to serve as an electrode for a light-emitting device. One such material commonly used as a transparent electrode in flat panel displays is indium tin oxide (ITO). However, ITO does not have a high enough conductivity to drive a bright and fast-responding large area display. While thin-film transistors may be employed to compensate for the low conductivity of ITO, such transistors are expensive and difficult to manufacture. Moreover, ITO lacks chemical stability with respect to certain electroluminescent application. Thus, while ITO may be sufficient for current flat panel display applications, necessary reliance on ITO highlights the problems with current electroluminescent configurations.

Even if an optically transparent and inert material may be found having sufficient conductivity to drive a bright and fast-responding large area display of the above configuration, it should be evident that the electroluminescent layer must also function as a spacer to separate the electrode layers. Thus, the electroluminescent layer must be pinhole free to prevent shorting between the electrode layers. In addition, the electroluminescent layer 16 must have a uniform thickness of about 1000 to about 2000 angstroms. In other words, the electron-injection interface 14 must be substantially parallel to the hole-injection interface 18. Otherwise, uneven emission output may result. Only a few materials can meet these requirements in order to serve as the electroluminescent layer. Further, it would be difficult to produce a plurality of devices such as that illustrated in FIG. 1 for use as color pixels for the display. Currently, there is no technique that can satisfactorily produce colored pinhole-free pixels having uniform thickness over a large area.

FIG. 2 schematically illustrates in simplified cross-sectional view of an inventive electroluminescent device. The device 30 is constructed from a layered structure on a substrate 32 having a cavity 34 extending through the layered structure. The layered structure comprises a hole-injection electrode layer 36, a dielectric layer 38 and an electron-injection electrode layer 40, wherein the dielectric layer is interposed between the hole-injection and electron-injection electrode layers. As shown, the hole-injection electrode layer 36 is the closest layer of the layered structure to the substrate. However, this is not a requirement, and the order of stacking for the layered structure may be reversed. That is, the electron-injection electrode layer may be the closest layer of the layered structure to the substrate. The cavity 34 extends from opening 48 entirely through the layered structure and terminates at the substrate 32. The cavity 34 is generally in the shape of a cylinder, i.e., the cross-sectional area of the cavity is constant along its longitudinal axis. As a result the cavity has an interior surface comprising of a hole-injection electrode region 42, a dielectric region 44 and an electron-injection electrode region 46. An electroluminescent coating material 50 is shown in general conformal contact with each region of the interior cavity surface. Conformal contact is preferred with each region of the interior cavity. At a minimum, however, the electroluminescent coating material must be provided electrical contact with both electrode regions of the interior cavity surface.

In operation, each electrode layer is connected to a power supply 52 that produces a voltage difference between the electrode layers. As a result, electrons are injected from the electron-injection electrode layer 40 into the electroluminescent coating material 38, and holes are injected from the hole-injection electrode layer 36 into the electroluminescent coating material 38. When the electrons and the holes combine, visible electromagnetic radiation is emitted by the electroluminescent coating material between the electrode regions, i.e., adjacent to the dielectric layer as indicated at 39. Once emitted, the radiation is transmitted through either the substrate 32, preferably the cavity opening 48, or both. It should be evident that this configuration does not require either of the electrode layers to be transparent for, device operability. It should be further evident that this configuration may be adapted to provide a double sided electroluminescent display device, i.e., a device that can be viewed from either of the electron-injection or the hole-injection electrode layer sides.

FIG. 3 schematically illustrates in simplified cross-sectional view of another version of the inventive electroluminescent device. Like the device illustrated in FIG. 2, this device 30 also has a layered structure. The device 30 comprises a hole-injection electrode layer 36, a dielectric layer 38 and an electron-injection electrode layer 40, wherein the dielectric layer is interposed between the hole-injection and electron-injection electrode layers. Unlike the device illustrated in FIG. 2, the electron-injection electrode layer 40 serves as a substrate for the electroluminescent device. The device also requires a cavity 34 that extends through the dielectric layer and at least one of the electrode layers; in this case, the cavity extends from opening 48 through the hole-injection electrode layer 36 and the dielectric layer 38 and terminates at the electron-injection electrode layer 40. As a result the cavity has an interior surface comprising a hole-injection electrode region 42, a dielectric region 44, an electron-injection electrode region 46. In this case, the cavity 34 is in the shape of a truncated cone. That is, the cross-sectional area of the cavity decreases as the cavity extends from the opening through the electron-injection electrode layer and the dielectric layer to the hole-injection electrode layer. An electroluminescent coating material 50 is shown filling the cavity and, as a result, exhibiting conformal contact with each region of the interior cavity surface. In addition, the coating material is also shown coating a non-cavity surface 47 of the hole-injection layer.

Like other embodiments of the inventive device, each electrode layer is connected to a power supply 52 that produces a voltage difference between the electrode layers. As a result, electrons and holes are injected into the electroluminescent coating material 50 and combined, resulting in emission of visible electromagnetic radiation from the electroluminescent coating material between the electrode regions, i.e., adjacent to the dielectric layer as indicated at 39. Once emitted, the radiation is transmitted through preferably the cavity opening 48. Due to the shape of this cavity, emitted electromagnetic radiation is less likely to be internally scattered and/or absorbed within the cavity than the cylindrically-shaped cavity of the device of FIG. 2. Other suitable cavity shapes include, but are not limited to, hemispherical, pyramidal, cubic, conical and hyperboloidal.

Figure 4:
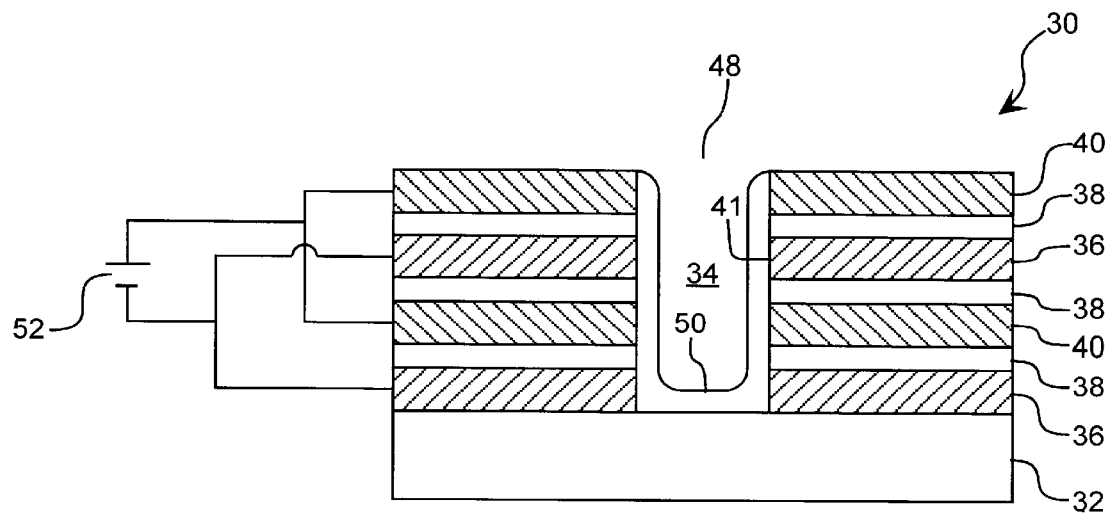
FIG. 4 schematically illustrates in simplified cross-sectional view still another electroluminescent device of the invention comprising a layered structure having a plurality of hole-injecting and electron-injection electrode layers in alternating stacking order with a dielectric layer between each electrode layer. The layered structure is located on a substrate, and a cavity extends through the layered structure. The cavity has an interior surface comprising a plurality of hole-injection electrode regions, dielectric regions and electron-injection electrode regions. An electroluminescent material coating is shown in conformal and electrical contact with each electrode region of the interior cavity surface.

For either of the inventive devices illustrated above, electroluminescence performance may be improved by providing one or more additional electrode layers. FIG. 4 schematically illustrates in simplified cross-sectional view of still another version of the inventive electroluminescent device that represents such an improvement. Like the device illustrated in FIG. 2, device 30 is constructed from a layered structure on a substrate 32 and a cavity 34 extending through the layered structure. However, the layered structure comprises two hole-injection electrode layers each indicated at 36, two electron-injection electrode layers each indicated at 40, and three dielectric layers each indicated at 38. The electrode layers are arranged in alternating stacking order, i.e., the nearest electrode layer to an electron-injection electrode layer is a hole-injection layer and vice versa. Each dielectric layer 38 is interposed between at least one hole-injection and at least one electron-injection electrode layer. The cavity 34 extends from opening 48 entirely through the layered structure and terminates at the substrate 32. As a result the cavity has an interior surface 41 that exposes a portion of each layer. An electroluminescent coating material 50 is shown in general conformal contact with each region of the interior cavity surface 41. As is the case with any of the electroluminescent devices described herein, each cavity may have a cross-sectional diameter from about 1 to about 50 micrometers, more preferably from about 3 to about 12 micrometers. The depth of the cavity must be sufficient to expose a surface for each electrode and is generally about 500 to about 10,000 angstroms.

In operation, each electrode layer is connected to a power supply 52 that produces a voltage difference between the electrode layers. As a result, electrons are injected from each electron-injection electrode layer 40 into the electroluminescent coating material 50, and holes are injected from each hole-injection electrode layer 36 into the electroluminescent coating material 50. When the electrons and the holes combine, visible electromagnetic radiation is emitted by the electroluminescent coating material between the electrode regions, i.e., adjacent to each dielectric layer as indicated at 39. It should be evident, then, that this device allows each cavity to provide greater electroluminescence than that illustrated in FIG. 2.

For any of the inventive electroluminescent devices, the substrate may be comprised of any of a number of materials depending on the desired use for the device. For example, the electroluminescent device may be formed on a silicon substrate that contains microcircuitry, in which case, the electroluminescent device represents an integrated portion of a microcircuitry-driven device. As another example, if the emitted radiation is to be transmitted through the substrate, the substrate must be transparent to the emitted radiation. Various ceramic and polymeric materials have sufficient optical transparency for transmitting visible emitted radiation. These substrate materials may be crystalline or amorphous. Examples of transparent ceramics include, but are not limited to, silicon dioxide, aluminum oxide, zirconium oxide, sodium chloride, diamond and various silicon-based glasses. Examples of transparent polymeric materials for transmitting visible emitted radiation include, but are not limited to, polycarbonate, polyethylene, polypropylene, polyester, polyimide, polyamides, polyacrylates and polymethacryates. While many materials exhibit a certain amount of flexibility, polymeric substrates are preferred if a flexible substrate is desired. Optionally, an insulating layer (not shown) may be interposed between the substrate and the layered structure. Further, the substrate may be detachable from the layered structure.

The electron-injection electrode layer may be composed of any suitable material capable of injecting electrons into the electroluminescent material. Various metallic, polymeric, ceramic and semiconducting materials may be capable of injecting electrons. In general, metallic materials are preferred because of their high electrical conductivity. As a result, an electron-injection electrode layer formed from a metallic material may be as thin as about 200 angstroms. To ensure electrical continuity, it is preferred that the electron-injection electrode layer have a thickness of at least about 400 angstroms. Typically, the electron-injection electrode layer has a thickness of about 200 to about 10,000 angstroms, more preferably about 400 to about 2000 angstroms. Suitable metals for use as an electron-injection electrode material include lithium, beryllium, magnesium, calcium, strontium, barium, boron, aluminum, gallium, indium, silver and alloys thereof.

Similarly, the hole-injection electrode layer may be composed of any suitable material capable of injecting holes into the electroluminescent material. Various metallic, polymeric, ceramic and semiconducting materials may be capable of injecting holes. Again, metallic materials are preferred because of their high electrical conductivity. Like the metallic electron-injection electrode layer, a metallic hole-injection electrode layer typically has a thickness of about 200 to about 10,000 angstroms, more preferably about 400 to about 2000 angstroms. Gold and copper are particularly suitable for use as a hole-injection electrode material due to their high conductivity and chemical inertness. Other metals suitable for use as a hole-injection electrode material include, but are not limited to, nickel, palladium, platinum, chromium, molybdenum, tungsten, manganese, nickel, cobalt, metal oxides and combinations and alloys thereof. However, certain conductive polymeric materials have also been found to exhibit excellent hole-injection properties. These polymeric materials include, but are not limited to polyaniline, polypyrrole and poly(3,4-ethylenedioxy-2,5-thiophene). In addition, certain ceramic materials such as conductive chalcogenides, e.g., metal oxides, mixed metal oxides and metal sulfides and mixed metal sulfides may also be suitable. It should be evident that any electrode layer may be constructed as a laminate, composite or mixture of materials.

The dielectric layer may be composed of any suitable material capable of serving as a barrier between the electrodes to provide an electrical barrier and to prevent electrical shorting between the electrode layers. Thus, the dielectric layer should be substantially pinhole free and composed from a high-resistivity material having an electrical resistivity no less than about $10^8$ ohm-cm, preferably no less than about $10^{12}$ ohm-cm. Suitable high-resistivity materials include, but are not limited to, silicon nitride, boron nitride, aluminum nitride, silicon oxide, aluminum oxide, polyimide, polyvinylidene fluoride, and paralene. Moreover, in order to reduce the overall thickness of the electroluminescent device, it is preferred that the dielectric layer does not exceed about 1 micrometer in thickness. A dielectric layer composed of such materials may have a thickness of about 100 to about 5000 angstroms, more preferably about 500 to about 2000 angstroms.

One of the advantages for providing a thin dielectric layer relates electroluminescent efficiency and power consumption. A thin dielectric layer reduces the distance between the electrodes and therefore also reduces the voltage needed to generate electroluminescence. However, dielectric materials may break down if excessive voltage is applied. Thus, for an inventive electroluminescent device employing an electroluminescent material that emits photons when an operating voltage is applied between the hole-injection and the electron-injection electrode layers, the dielectric layer must have sufficient dielectric strength for its thickness to withstand the operating voltage. To provide a more robust device configuration, it is preferred that the dielectric layer have sufficient dielectric strength for its thickness to withstand at least about 2 volts over the operating voltage. For example, if the device is constructed to provide emit light when a 5-volt potential is applied, the dielectric layer should be able to withstand at least about 7 volts.

For any of the inventive electroluminescent devices, the electroluminescent coating material may comprise any number of organic or inorganic compounds or mixtures thereof. The material must contain at least one electroluminescent compound, typically organic, but on occasion may be inorganic. These electroluminescent compounds may comprise relatively simple organic molecules to complex polymers or copolymers. Examples of relatively simple organic luminescent molecules include, but are not limited to tris(8-hydroxyquinolinato)-aluminum and perylene. In the case of polymers or copolymers, the molecular structure may comprise a carbon-based or silicon-based backbone. The polymers and copolymers may be linear, branched, crosslinked or any combinations thereof, and may have a wide range of molecular weights from as low as about 5000 to more than 1,000,000. In the case of copolymers, the copolymers may be alternating, block, random, graft, or combinations thereof. Examples of suitable electroluminescent polymers useful in conjunction with the present invention include, but are not limited to, conjugated polymers such as, polyparaphenylenes, polythiophenes, polyphenylenevinylenes, polythienylvinylenes, polyfluorenes, 1,3,4-oxadiazole-containing polymers, and various derivatives and copolymers thereof. An exemplary electroluminescent polymer is an arylamine-substituted poly (arylene-vinylene) as described in co-pending U.S. patent application Ser. No. 09/619,372, for "Arylamine-Substituted Poly(Arylene Vinylenes) and Associated Methods of Preparation and Use," filed on even date herewith and also assigned to SRI International (Menlo Park, Calif.). Such polymers have the general structure of formula (I)

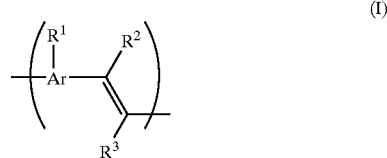

(I)

wherein:
   Ar is arylene, heteroarylene, substituted arylene or substituted heteroarylene containing one to three aromatic rings;
   $R^1$ is the arylamine substituent and is of the formula —$Ar^1$—$N(R^4R^5)$ wherein $Ar^1$ is as defined for Ar and $R^4$ and $R^5$ are independently hydrocarbyl, substituted hydrocarbyl, heteroatom-containing hydrocarbyl, or substituted heteroatom-containing hydrocarbyl; and
   $R^2$ and $R^3$ are independently selected from the group consisting of hydrido, halo, cyano, hydrocarbyl, substituted hydrocarbyl, heteroatom-containing hydrocarbyl, and substituted heteroatom-containing hydrocarbyl, or $R^2$ and $R^3$ may together form a triple bond.
   Preferred moieties are as follows:
   Ar may be a five-membered or six-membered arylene, heteroarylene, substituted arylene or substituted heteroarylene group, or may contain one to three such groups, either fused or linked. Preferably, Ar is comprised of one or two aromatic rings, and is most preferably comprised of a single aromatic ring that is five-membered or six-membered arylene, heteroarylene, substituted arylene or substituted heteroarylene. $Ar_1$, the arylene linking moiety in the arylamine substituent, is defined in the same way.

The substituents $R^2$ and $R^3$ are generally hydrido but may also be halo (particularly chloro or fluoro) or cyano, or substituted or unsubstituted alkyl, alkoxy, alkenyl, alkynyl, aryl and heteroaryl.

$R^4$ and $R^5$ may the same or different and, as noted, are hydrocarbyl, substituted hydrocarbyl, heteroatom-containing hydrocarbyl, or substituted heteroatom-containing hydrocarbyl. For example, $R^4$ and $R^5$ may be alkyl, alkoxy-substituted alkyl, polyether-substituted alkyl, nitro-substituted alkyl, halo-substituted alkyl, aryl, alkoxy-substituted aryl, polyether-substituted aryl, nitro-substituted aryl, halo-substituted aryl, heteroaryl, alkoxy-substituted heteroaryl, polyether-substituted heteroaryl, nitro-substituted heteroaryl, halo-substituted heteroaryl, and the like. Particularly preferred substituents are aryl, e.g., phenyl, alkoxy-substituted phenyl (particularly lower alkoxy-substituted phenyl such as methoxyphenyl), polyether-substituted phenyl (particularly phenyl substituted with a —$CH_2(OCH_2CH_2)_nOCH_3$ or —$(OCH_2CH_2)_nOCH_3$ group where n is generally 1 to 12, preferably 1 to 6, most preferably 1 to 3), and halo-substituted phenyl (particularly fluorinated or chlorinated phenyl).

In a preferred embodiment, the arylamine-substituted arylene-vinylene polymer contains monomer units having the general structure of formula (II)

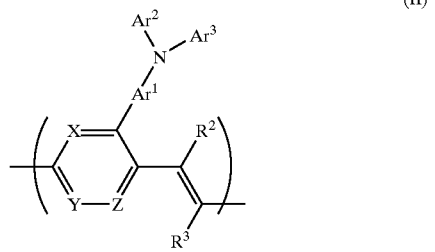

(II)

wherein:
X, Y and Z are independently selected from the group consisting of N, CH and $CR^6$ wherein $R^6$ is halo, cyano, alkyl, substituted alkyl, heteroatom-containing alkyl, aryl, heteroaryl, substituted aryl, or substituted heteroaryl, or wherein two $R^6$ moieties on adjacent carbon atoms may be linked to form an additional cyclic group;
$Ar^1$ is as defined above;
$Ar^2$ and $Ar^3$ are independently selected from the group consisting of aryl, heteroaryl, substituted aryl and substituted heteroaryl containing one or two aromatic rings; and
$R^2$ and $R^3$ are as defined above.

In formula (II), the polymer is a poly(phenylene vinylene) derivative when X, Y and Z are all CH. When at least one of X, Y and Z is N, the aromatic ring will be, for example, substituted or unsubstituted pyridinyl, pyridazinyl, pyrimidinyl, pyrazinyl, 1,2,4-triazinyl, or 1,2,3-triazinyl. Most preferably, one of X, Y and Z is CH and the other two are either CH or $CR^6$, wherein $R^6$ is optimally heteroatom-containing alkyl, preferably alkoxy, and most preferably a polyether substituent —$CH_2(OCH_2CH_2)_nOCH_3$ or —$(OCH_2CH_2)_nOCH_3$ group where n is generally 1 to 12, preferably 1 to 6, most preferably 1 to 3, as above.

The polymer may be a homopolymer or a copolymer with at least one additional type of monomer unit. Preferably, if the polymer is a copolymer, the additional monomer units are also arylene-vinylene monomer units, for example having the structure (III)

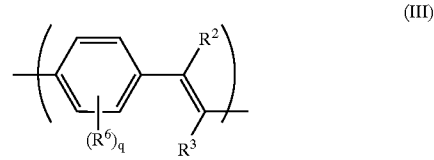

(III)

wherein $R^2$, $R^3$ and $R^6$ are as defined previously and q is an integer in the range of zero to 4 inclusive.

Examples of specific polymers having the structure of formula (I) are poly(2-(4-diphenylamino-phenyl)-1,4-phenylene vinylene and poly(2-(3-diphenylaminophenyl)-1,4-phenylene vinylene.

In another embodiment, the invention provides a method for forming the above described electroluminescent device. The method involves first providing a layered structure comprising a hole-injection and electron-injection electrode layers and a dielectric layer interposed therebetween. The layered structure has a cavity extending through the dielectric layer and at least one of the electrode layers such an interior cavity surface is exposed comprising a hole-injection electrode region, an electron-injection electrode region and a dielectric region. The method also involves coating the interior cavity surface with an electroluminescent coating material to provide the electroluminescent material electrical contact with the hole-injection and electron-injection electrode regions.

FIG. 5 illustrates one method for forming an electroluminescent device as a layered structure on a substrate. FIG. 5A illustrates the deposition of a hole-injection electrode layer 36 on a substrate 32, FIG. 5B illustrates the deposition of a dielectric layer 38 on the hole-injection electrode layer 36, and FIG. 5C illustrates the deposition of an electron-injection layer 40 on the dielectric layer 38, thereby forming a layered structure. It is to be noted that the order of layer deposition may be reversed, i.e., the electron-injection electrode layer may be initially deposited on the substrate, the dielectric layer is then deposited on the electron-injection layer and the hole-injection electrode layer is then deposited on the dielectric layer.

It is also to be noted that a variety of techniques may be used to deposit each layer. Such deposition techniques include, but are not limited to, evaporation, sputtering, chemical vapor deposition, electroplating, spin coating and other techniques familiar to one of ordinary skill in the art of semiconductor fabrication. In addition, it is to be noted that the deposition technique must be chosen according to the layer material. For example, metals may be deposited by evaporation, sputtering, electroplating, chemical vapor deposition, etc.

In order to achieve the preferred thickness for each layer, vacuum deposition technology is generally preferred. Such vacuum processes include, but are not limited to, cathodic arc physical vapor deposition, electron-beam evaporation, enhanced arc physical vapor deposition, chemical vapor deposition, magnetronic sputtering, molecular beam epitaxy, combinations of such techniques and a variety of other techniques known to one of ordinary skill in the art. One of ordinary skill in the art will also recognize that chemical vapor deposition is particularly suited for forming dielectric layer materials such as silicon nitride. Chemical vapor deposition usually involves heating a substrate surface to a sufficiently high temperature to decompose gaseous organic species to form the desired film. Such heating may preclude the use of plastic as a surface on which the film is deposited. Physical vapor deposition, on the other hand, does not necessarily exclude plastics as a substrate. In addition, some substrate heating may be employed in physical vapor deposition to promote film adhesion. It is also to be noted that vacuum deposition may be required if a reactive metal such as magnesium or calcium is used as an electrode layer material.

Figure 5A:
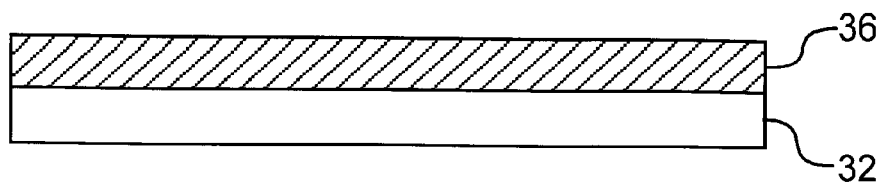
FIGS. 5A, 5B, 5C, 5D, 5E, 5F, 5G, 5H and 5I, collectively referred to as FIG. 5, illustrate a method for producing an electroluminescent device.
Figure 5B:
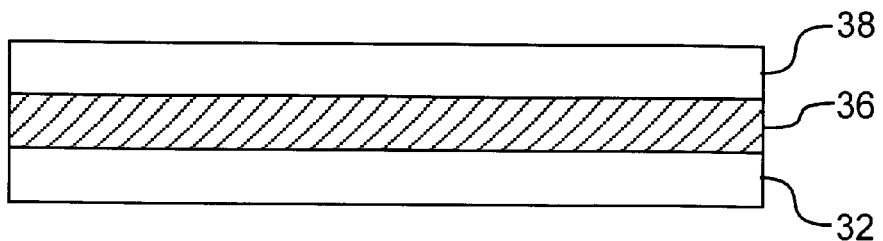
Figure 5C:
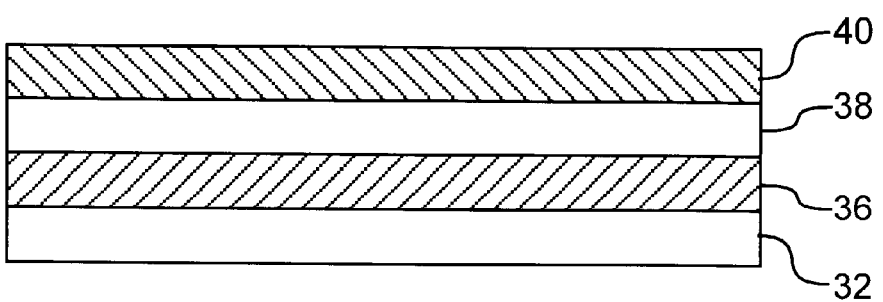
Figure 5D:
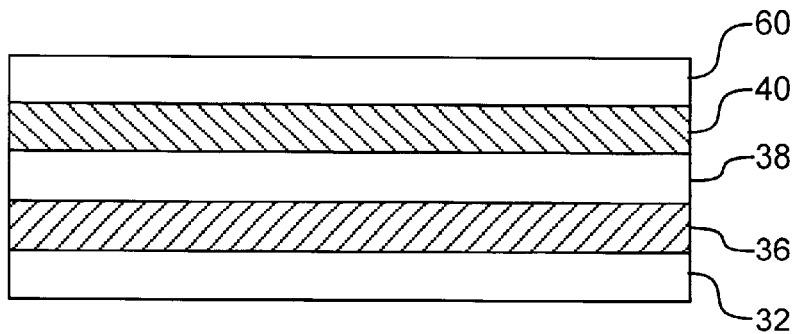
Figure 5E:
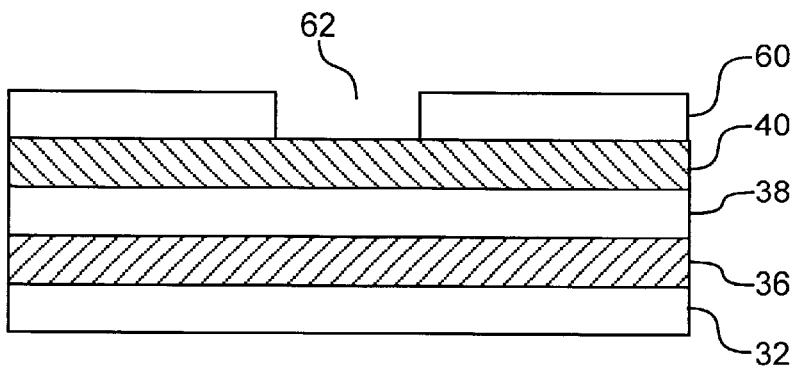
Figure 5F:
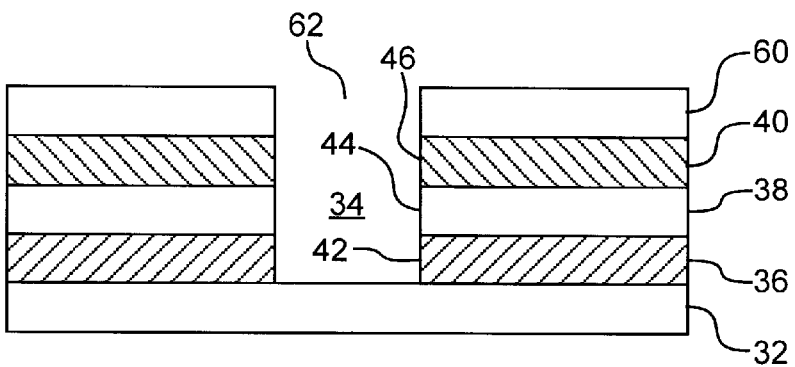
Figure 5G:
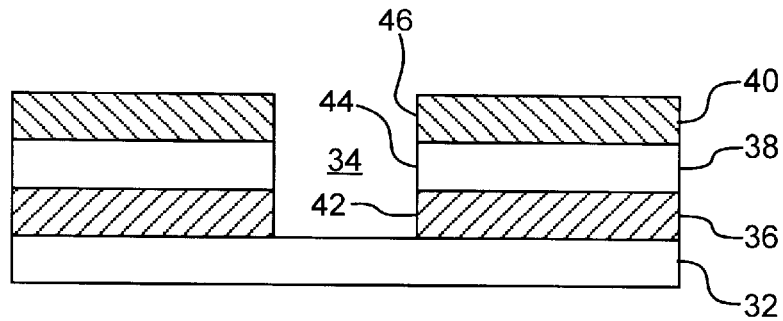

FIGS. 5D, 5E and 5F illustrate the formation of a cavity through the electrode and dielectric layers by using a lithographic and etching technique. FIG. 5D illustrates the deposition of a resist layer 60 on the electron-injection electrode layer 40 of the layered structure formed in FIG. 5C. The resist is then developed in a pattern, as illustrated in FIG. 5E to provide an opening 62 through which an etchant may be applied to an exterior surface of the layered structure, in this case, the exterior surface of the electron-injection electrode layer. Once etchant is applied to the layered structure, cavity 34, as shown in FIG. 5F, is formed extending from opening 42 entirely through the layered structure and terminates at the substrate 32 comprising a hole-injection electrode region 42, a dielectric region 44 and an electron-injection electrode region 46. While FIG. 5F illustrates that cavity 34 having a cylindrical shape can be formed, it is also possible to form cavities of other shapes by selective application of one or more isotropic or anisotropic etchants to the layered structure. The etchant may be a gas, liquid, solid or a combination thereof or require an additional energy source such as electromagnetic radiation or electrons. That is, either dry (e.g., plasma) or wet (e.g. chemical) etching techniques may be used. It should be evident that the etchant must be able to etch through at least one electrode material and the dielectric material in order to form the interior cavity surface having the hole-injection electrode region, the dielectric region and the electron-injection electrode region. In any case, one of ordinary skill in the art is capable of selecting and applying an etchant to form a cavity of desired geometry. Optionally, the resist is removed, as shown in FIG. 5G before an electroluminescent coating is applied to the interior cavity surface. It should be evident that the above described patterning and etching processes may carried out using lithographic techniques generally known in the field of semiconductor processing as described in Sze (1983), "Lithography," VSLI Technology, McGraw-Hill Book Company. As another option, the interior surface of the cavity may be modified before the electroluminescent material is applied. As the cavity surface may easily oxidize or otherwise become contaminated before the electroluminescent coating material is applied, surface treatments may be employed immediately prior to the application of the electroluminescent material. For example of surface treatments include, but are not limited to, drying cleaning (e.g., exposure to plasma), wet etching, solvent cleaning. In addition, the cavity surface may be modified by attaching a surface-modifying moiety to provide for improved adhesion between the cavity surface and the electroluminescent coating. Cavity surface modification may also involve providing a material or coating that enhances hole and/or electron transport between the electrodes and the electroluminescent coating.

Figure 5H:
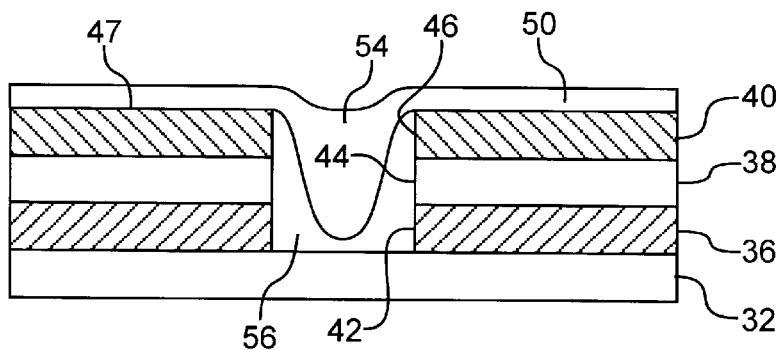
Figure 5I:
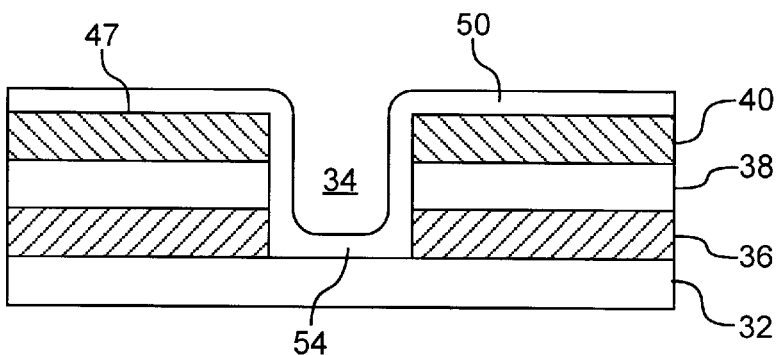
Figure 6A:
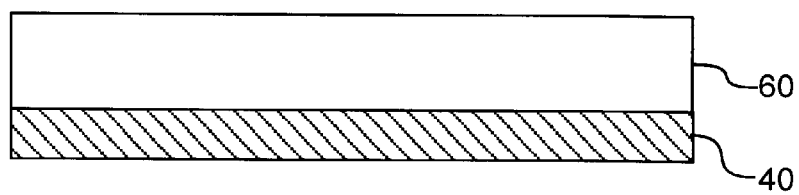
FIGS. 6A, 6B, 6C, 6D and 6E collectively referred to as FIG. 6, illustrate an alternative method for making a cavity-containing layered structure of a luminescent device.
Figure 6B:
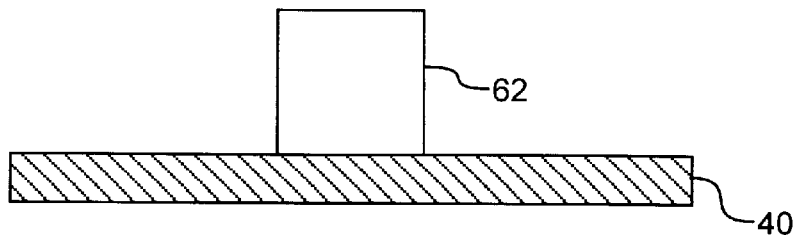
Figure 6C:
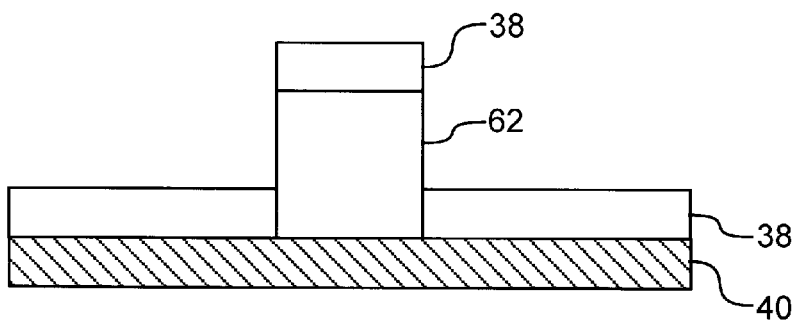
Figure 6D:
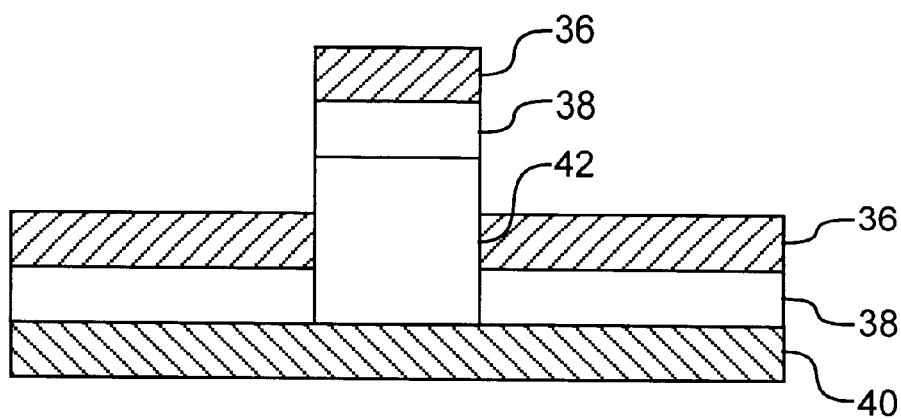
Figure 6E:
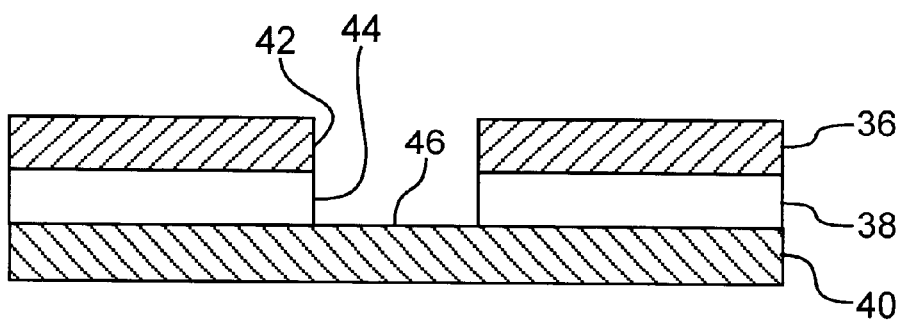

The electroluminescent coating material may be applied to the interior cavity surface through any of a number of techniques that depend on the material properties of the electroluminescent material itself. When the coating material is polymeric in nature, the coating material may be formed in situ on the cavity surface or applied by solvent casting, spin coating, spray coating, printing or other techniques to the cavity surface. FIGS. 5H and 5I illustrate the application of an electroluminescent coating material to the interior surface of the cavity such to achieve conformal contact between the coating material and the interior surface. FIG. 5G illustrates a coating technique in which the coating material 50 is applied as a film over the exterior surface 47 of the electron-injection electrode layer 40 of the layered structure illustrated in FIG. 5F. As shown, a portion 54 of the electroluminescent material fills the cavity. However, such application of electroluminescent material, as illustrated in FIG. 5F, may result in void space 56 between the electroluminescent coating material and the interior cavity surface. The void may be eliminated, as shown in FIG. 5G, by subjecting the coating material to heat and/or vacuum, particularly when the coating material is a polymeric material.

FIG. 6 illustrates another method in which the electroluminescent device may be formed. FIGS. 6A and 6B illustrate the formation of a sacrificial member in the shape of a desired cavity of the layered structure of a luminescent device. In FIG. 6A, an electrode layer 40, an electron-injection layer in this case, in the form of a substrate is coated with a photoresist 60. The resist is then developed in a pattern, as illustrated in FIG. 6B, to provide a sacrificial member 62 in the shape of a desired cavity. FIG. 6C illustrates the deposition of a dielectric layer 38 on the electron-injection electrode layer 40 and around the sacrificial member 62. Similarly, FIG. 6D illustrates the deposition of a hole-injection electrode layer 36 on the dielectric layer 38 and around the sacrificial member 62. As is the case illustrated in FIG. 5, it is to be noted that the order of layer deposition may be reversed, i.e., the sacrificial member may be formed on an electrode-injection electrode layer, followed by depositing the dielectric layer on the electron-injection electrode layer and depositing the hole-injection electrode layer on the dielectric layer. When the sacrificial member is removed, a layered structure is formed having a cavity through the hole-injection and the dielectric layer. As shown in FIG. 6E, the interior surface of the cavity of the layered structure is composed of a hole-injection electrode region 42, a dielectric layer region 44 and an electron-injection electrode region 46. The interior surface of the cavity of the layered structure is now ready to be coated with an electroluminescent coating material.

In another embodiment, the invention provides an electroluminescent display device, comprising a layered structure as described above, a plurality of cavities each extending through a portion of the layered structure such that each cavity has an interior cavity surface comprising a hole-injection electrode region, an electron-injection electrode region and a dielectric region; and the electroluminescent material in electrical contact with the hole-injection and electron-injection electrode regions of each interior cavity surface. Preferably, the plurality of cavities is arranged in an array.

It is desirable to produce a red, green and blue pattern for color display applications. Generally, it will be apparent to those skilled in the art that to fabricate a device useful for a multicolor display, the positions of the colored cavities must correspond to associated subpixels of the display since a pixel in an electroluminescent display device comprises three subpixels, typically red, green and blue. Accordingly, each cavity may be filled with an electroluminescent material capable of emitting one of these three colors. Alternatively, one or more emission modifiers may be added to the same electroluminescent material in each cavity. Suitable emission modifiers include, but are not limited to, organic and organometallic luminescent dyes such as 2-methyl-8-hydroquinoline aluminum, 8-hydroquinoline aluminum, coumarins, acridines, quinolone, carbostyryls, flurols, phenoxazenes, rhodamines, and fluoresceins. In selecting a suitable light-emissive dye, one or ordinary skill in the art will recognize that color and luminescent efficiency are two important factors which can be determined through routine experimentation. Moreover, emission modifiers may themselves be polymeric electroluminescent materials. For example poly(1,4-phenylene vinylene), poly(2-methoxy-5-(2-ethylhexoxy)-1,4-phenylene vinylene) and poly(9,9-dioctyl-2,7-fluorene) may be adapted to emit green, orange-red and blue light, respectively. Other suitable modifiers include, but are not limited to, pigments and light absorbing dyes such as phthalocyanines, such as Pigment Blue 15, nickel phthalocyanine, chloroaluminum phthalocyanine, hydroxy aluminum phthalocyanine, vanadyl phthalocyanine, titanyl phthalocyanine, and titanyl tetrafluorophthalocyanine; isoindolinones, such as Pigment Yellow 110 and Pigment Yellow 173; isoindolines, such as Pigment Yellow 139 and Pigment Yellow 185; benzimidazolones, such as Pigment Yellow 151, Pigment Yellow 154, Pigment Yellow 175, Pigment Yellow 194, Pigment Orange 36, Pigment Orange 62, Pigment Red 175, and Pigment Red 208; quinophthalones, such as Pigment Yellow 138; quinacridones, such as Pigment Red 122, Pigment Red 202, and Pigment Violet 19; perylenes, such as Pigment Red 123, Pigment Red 149, Pigment 179, Pigment Red 224, and Pigment Violet 29; dioxazines, such as Pigment Violet 23; thioindigos, such as Pigment Red 88, and Pigment Violet 38; epindolidiones, such as 2,8-difluoroepindolidione; anthanthrones, such as Pigment Red 168; isoviolanthrones, such as isoviolanthrone; indanthrones, such as Pigment Blue 60; imidazobenzimidazolones, such as Pigment Yellow 192; pyrazoloquinazolones, such as Pigment Orange 67; diketopyrrolopyrroles, such as Pigment Red 254, Irgazin DPP RubinTR, Cromophtal DPP OrangeTR; Chromophtal DPP Flame Red FP (all of Ciba-Geigy); and bisaminoanthrones, such as Pigment Red 177. Of the aforementioned dyes, light-emitting dyes are preferred over light absorbing or pigment containing dyes. These modifiers can be added either by employing ordinary lithographic techniques or by using an inkjet technology to selectively deposit an emission modifier at desired cavities. If a photocurable photoresist technique is employed in order to modify an electroluminescent polymeric material, it may be desirable to crosslink the polymeric material in order to dimensionally stabilize the polymeric material and to prevent damage thereto.

Variations on of the present invention will be apparent to those knowledgeable in the field of electroluminescent devices. For example, while the layered structure having a cavity may be formed by ordinary lithographic and etching techniques, other techniques such as laser ablation may also be employed, either as an alternative or in addition, to remove material from the layered structure. The present invention also allows the incorporation of known aspects of electroluminescent display device design such as interdigitated electrodes. It should also be noted that additional layers may be formed between each layer to promote interlayer adhesion or to improve electrical properties such as electron and/or hole transport.

One of ordinary skill in the art will also recognize other considerations such as packaging and electronics are also an essential consideration for any display. Reactive metals and luminescent materials used in these displays are subject to attack by moisture and air. Therefore, the displays must be packaged accordingly. Such packaging may involve lamination or other technologies known in the art. Device electronics may include commercially available systems appropriate to any desired display design.

It is to be understood that while the invention has been described in conjunction with the preferred specific embodiments thereof, that the foregoing description and the examples that follow are intended to illustrate and not limit the scope of the invention. Other aspects, advantages and modifications within the scope of the invention will be apparent to those skilled in the art to which the invention pertains.

All patents, patent applications, and publications mentioned herein are hereby incorporated by reference in their entireties.

EXPERIMENTAL

The practice of the present invention employs, unless otherwise indicated, conventional techniques of semiconductor processing, and the like, which are within the skill of the art. Such techniques are explained fully in the pertinent texts and literature. See, e.g., *VLSI Technology*, S. M. Sze, ed. (New York: McGraw-Hill Book Company, 1983) and Sorab K. Ghandi, *VSLI Fabrication Principles*, $2^{nd}$ Ed. (New York: John Wiley & Sons, 1994). Preparation of suitable electroluminescent polymers also employs conventional techniques of polymer chemistry and the like, which are within the skill of the art; see, e.g., *Vogel's Textbook of Practical Organic Chemistry*, $5^{th}$ Ed., B. S. Furniss et al., eds. (New York: Longman Scientific and Technical, 1989); A. Kraft et al. (1998) *Angew. Chem. Int. Ed.* 37:402–428; and T. A. Skotheim et al., "*Electroresponsive Molecular and Polymeric Systems*," (New York: Marcel Dekker, 1991).

Examples 1–6 describe an edge-emitting electroluminescent device built on a flat substrate. A hole injection electrode, a dielectric layer, and electron injection electrode were coated on the substrate. Then, the electron injection electrode and dielectric layer were selectively etched off to form an array of cavities. An electroluminescent polymer was coated on the wall of the cavities. When a voltage bias was applied between the hole and electron injection electrodes, light was emitted from the cavities. In each example, efforts have been made to ensure accuracy with respect to numbers used (e.g., thicknesses, cavity dimensions, drying temperature, etc.) but some experimental error and deviation should be accounted for. Examples 7–10 describe methods for preparing arylamine-substituted poly (arylene vinylenes) useful in conjunction with the cavity-emission devices of the invention.

EXAMPLE 1

A silicon wafer substrate was coated with 1 micrometer thick silicon dioxide by the thermal oxidation of silicon. A layer of 1500 angstrom thick gold was sputtered on the silicon dioxide forming a hole-injection electrode layer. A photoresist layer was coated on gold and patterned. The gold coating not covered by the resist was etched off, resulting in a patterned hole-injection electrode layer. Then the masking photoresist layer was removed.

After the bole-injection electrode layer was formed, a 1500 angstrom thick dielectric layer of silicon nitride was deposited on the patterned hole-injection electrode layer. The silicon nitride was deposited using the plasma enhanced chemical vapor deposition method. This silicon nitride dielectric layer coating formed in two stages to reduce defects. First, about 750 angstroms of silicon nitride was deposited on the hole-injection layer. Then, the dielectric layer surface was cleaned, and another 750 angstroms silicon nitride was deposited on the cleaned surface.

A lift-off method was used then used to pattern the electron injection electrode on the dielectric layer. Sacrificial photoresist layer was coated in a pattern patterned on the dielectric layer. Next, a layer of 1500 angstrom aluminum was deposited on the photoresist-patterned surface by vacuum electron evaporation. When the photoresist was removed, the aluminum on the photoresist was lifted off while the aluminum on the dielectric layer remained. The dielectric layer not covered by the aluminum pattern was removed through reactive ion etching method, forming cavities 0.2–0.4 micrometers in depth, 6 micrometers in diameter. Then, a precursor polymer, poly(p-xylylidene tetrahydrothiophenium tetrafluoroborate), was cast in the cavities by applying the polymer solution in acetonitrile and allowing the solvent to evaporate. The precursor was then converted to poly(1,4-phenylene vinylene) at 150° C. for 3 hours in a dry box. As a result, an electroluminescent display device is formed.

A voltage was applied between the gold and aluminum electrode layers, with the gold as the anode. At about 3V and higher, green light was emitted from the cavities. The light emission was fairly uniform to the naked eye.

EXAMPLE 2

The electroluminescent device of the Example 1 was produced except that the diameter of the microcavities was varied between 3 and 12 micrometers.

EXAMPLE 3

The electroluminescent device of the Example 1 was produced except that indium tin oxide coated glass was used in place of the gold/$SiO_2$ coated silicon wafer.

EXAMPLE 4

The electroluminescent device of the Example 1 was produced except that the dielectric spacer used a paralene polymer in place of silicon nitride.

EXAMPLE 5

The electroluminescent device of the Example 3 was produced except that the electroluminescent polymer was poly(2-methoxy-5-(2-ethylhexoxy)-1,4-phenylene vinylene), rather than poly(1,4-phenylene vinylene). The emitted light was orange-red.

EXAMPLE 6

The electroluminescent device of the Example 3 was produced except that the electroluminescent polymer was poly(9,9-dioctyl-2,7-fluorene), rather than poly(1,4-phenylene vinylene). The emitted light was blue.

EXAMPLE 7

This example describes preparation of an electroluminescent polymer useful as in conjunction with the cavity-emission electroluminescent devices of the invention:

(a) Synthesis of 2-(4-diphenylaminophenyl)-1,4-bis (chloromethyl)benzene

4-Diphenylamino-1-(4,4,5,5-tetramethyl-1,3,2-Dioxaborolan-2-yl)benzene (6.09 g) (prepared by successive reaction of 4-bromo-triphenylamine with butyllithium and 2-isopropoxy-4,4,5,5-tetramethyl-1,3,2-dioxaborolane), 2-bromo-1,4-bis(acetyloxymethyl)benzene (4.9 g), tetrakis (triphenylphosphine)-palladium(0) (0.15 g), toluene (15 mL), and an aqueous solution of sodium carbonate (2M, 25 mL) were mixed under argon. The resulting mixture was stirred at reflux for 2 days, cooled, and poured into water. The aqueous mixture was then extracted with ether. The etheral solution was washed with dilute HCl, brine, dried with magnesium sulfate, and evaporated. The residue was recrystallized in methanol to yield 5.70 g of 2-(4-diphenylamino-phenyl)-1,4-bis(acetyloxymethyl)benzene.

The resulting 2-(4-diphenylaminophenyl)-1,4-bis (acetyloxymethyl)benzene was hydrolyzed in a solution of sodium hydroxide (6 g) in ethanol/water (40 mL/20 mL). The resulting 2-(4-diphenylaminophenyl)-1,4-bis (hydroxymethyl)benzene was purified by recrystallization in toluene.

2-(4-Diphenylaminophenyl)-1,4-bis(hydroxymethyl) benzene (3.75 g) was reacted with excess amount of thionyl chloride in tetrahydrofuran. The crude product was recrystallized in hexanes to yield 1.5 g of 2-(4-diphenylaminophenyl)-1,4-bis(chloromethyl)benzene. $^1$H NMR (CDCl$_3$): δ=4.6 (4H), δ=7.0–7.4 (8H,), δ=7.5–7.6 (1H).

In a similar manner, 2-(3-diphenylaminophenyl)-1,4-bis (chloromethyl)benzene was synthesized.

(b) Synthesis of Poly(2-(4-diphenylaminophenyl)-1, 4-phenylene Vinylene)

A potassium t-butoxide solution in tetrahydrofuran (1M, 2 mL) was added in 10 seconds into a solution of 2-(4-diphenylaminophenyl)-1,4-bis(chloromethyl)benzene (0.70 g) in 50 mL of tetrahydrofuran under argon and vigorous stirring at 22° C. After stirring at 22° C. for 10 minutes, the solution temperature was raised to refluxing. Then, more potassium t-butoxide solution in tetrahydrofuran (1M, 4 mL) was added, and the solution stirred and refluxed for 1.5 hrs. Methanol (100 mL) was added to terminate the reaction. The polymer that precipitated from the mixture was collected by filtration, washed repeatedly with methanol, water, water/ methanol (1:1), and methanol. It was redissolved in chloroform, precipitated in methanol, and dried in vacuum to yield 0.43 g of bright yellow fibrous solid of poly(2-(4-diphenylaminophenyl)-1,4-phenylene vinylene). $^1$H NMR (CDCl$_3$): δ=7.0–7.4 (broad peaks).

EXAMPLE 8

Synthesis of Poly(2-(3-diphenylaminophenyl)-1,4-phenylene Vinylene)

A potassium t-butoxide solution in tetrahydrofuran (1M, 2 mL) was added in 10 seconds into a solution of 2-(3-diphenylaminophenyl)-1,4-bis(chloromethyl)benzene (0.70 g) in 50 mL of tetrahydrofuran under argon and vigorous stirring at 22° C. After stirring at 22° C. for 10 minutes, the solution temperature was raised to refluxing. Then, more potassium t-butoxide solution in tetrahydrofuran (1M, 4 mL) was added, and the solution stirred and refluxed for 1.5 hrs. Methanol (100 mL) was added to terminate the reaction. The polymer that precipitated from the mixture was collected by filtration, washed repeatedly with methanol, water, water/ methanol (1:1), and methanol. It was redissolved in chloroform, precipitated in methanol, and dried in vacuum to yield 0.41 g of bright yellow fibrous solid.

EXAMPLE 9

Synthesis of Poly{[2-(4-diphenylaminophenyl)-1,4-phenylene Vinylene)]-co-[2-(3-diphenylaminophenyl)-1,4-phenylene vinylene)]} (PMTPA-PPV)

A potassium t-butoxide solution in tetrahydrofuran (1M, 6 mL) was added in 10 seconds into a solution of 1,4-bis (chloromethyl)-2-(4-diphenylaminophenyl)benzene (0.35 g) and 1,4-bis(chloromethyl)-2-(3-diphenylaminophenyl) benzene (0.35 g) in 70 mL of 1,4-dioxane under argon and vigorous stirring at 95° C. The solution was stirred at reflux for 1 hr and cooled to 25° C. Methanol (100 mL) was added into the solution. The polymer that precipitated from the mixture was collected by filtration, washed repeatedly with methanol, water, water/methanol (1:1), and methanol. It was redissolved in chloroform, precipitated in methanol, and dried in vacuum to yield 0.35 g of bright yellow fibrous solid.

Thin films of PMTPA-PPV were cast from its solution in chlorobenzene.

EXAMPLE 10

Synthesis of Poly {[2-(4-diphenylaminophenyl)-1,4-phenylene Vinylene)]-co-[2-methoxy-5-(2-ethylhexyloxy)-1,4-phenylene Vinylene)]}

A potassium t-butoxide solution in tetrahydrofuran (1M, 10 mL) was added in 10 seconds into a solution of 1,4,-bis(chloromethyl)-2-(4-diphenylaminophenyl)benzene (0.5 g) and 1,4-bis(chloromethyl)-2-methoxy-5-(2-ethylhexyloxy) benzene (0.5 g) in 100 mL of 1,4-dioxane under argon and vigorous stirring at 95° C. The solution was stirred at reflux for 1 hr and cooled to 25° C. Methanol (100 mL) was added into the solution. The polymer that precipitated from the mixture was collected by filtration, washed repeatedly with methanol, water, water/methanol (1:1), and methanol. It was redissolved in tetrahydrofuran, precipitated in methanol, and dried in vacuum to yield 0.515 g of a bright orange fibrous solid.

What is claimed is:

1. An electroluminescent device, comprising a layered structure of
    a hole-injection electrode layer,
    an electron-injection electrode layer, and
    a dielectric layer interposed between the hole-injecting and electron-injecting electrode layers and
    a cavity extending through at least the dielectric layer and one of the electrode layers and having an interior cavity surface comprising a hole-injection electrode region, an electron-injection electrode region and a dielectric region,
    wherein an electroluminescent coating material is in electrical contact with the hole-injection and electron-injection electrode regions of the interior cavity surface.

2. The electroluminescent device of claim 1, wherein one of the electrode layers is a substrate.

3. The electroluminescent device of claim 1, wherein the layered structure is present on a substrate.

4. The electroluminescent device of claim 3, further comprising an insulating layer interposed between the substrate and the layered structure.

5. The electroluminescent device of claim 3 wherein the substrate is detachable from the layered structure.

6. The electroluminescent device of claim 3, wherein the substrate comprises a flexible material.

7. The electroluminescent device of claim 6, wherein the flexible material is a polymeric material.

8. The electroluminescent device of claim 3, wherein the substrate is transparent.

9. The electroluminescent device of claim 1, wherein the electroluminescent coating material comprises an electroluminescent polymer.

10. The electroluminescent device of claim 9, wherein the electroluminescent polymer is a conjugated polymer selected from the group consisting of polyparaphenylenes, polythiophenes, polyphenylenevinylenes, arylamine-substituted polyarylenevinylenes, polythienylvinylenes, polyfluorenes, and 1,3,4-oxadiazole-containing polymers.

11. The electroluminescent device of claim 10, wherein the electroluminescent polymer is an arylamine-substituted polyarylenevinylene.

12. The electroluminescent device of claim 9, wherein the electroluminescent material further comprises a surfactant.

13. The electroluminescent device of claim 1, wherein the electroluminescent material comprises a non-polymeric electroluminescent molecule.

14. The electroluminescent device of claim 13, wherein the non-polymeric electroluminescent molecule is tris(8-hydroxyquinolinato) aluminum or perylene.

15. The electroluminescent device of claim 13, wherein the non-polymeric electroluminescent molecule is inorganic.

16. The electroluminescent device of claim 15, further comprising an additional dielectric coating material interposed between the electroluminescent coating and at least one of the electrode regions of the interior cavity surface.

17. The electroluminescent device of claim 1, further comprising an additional coating material interposed between the electroluminescent coating material and at least one of the electrode regions of the interior surface, wherein the additional coating material enhances electron and/or hole injection.

18. The electroluminescent device of claim 1, wherein at least one electrode layer has a thickness of about 200 to about 2000 angstroms.

19. The electroluminescent device of claim 18, wherein the thickness is about 400 to about 1000 angstroms.

20. The electroluminescent device of claim 1, wherein the dielectric layer has a thickness of about 500 to about 2000 angstroms.

21. The electroluminescent device of claim 1, wherein the hole-injection electrode layer comprises a material selected from the group consisting of gold, copper, nickel, palladium, platinum, chromium, molybdenum, tungsten, manganese, cobalt, metal oxides, conducting polymers and combinations and alloys thereof.

22. The electroluminescent device of claim 1, wherein the electron-injection electrode layer comprises a material selected from the group consisting of lithium, strontium, barium beryllium, magnesium, calcium, boron, aluminum, gallium, indium and combinations and alloys thereof.

23. The electroluminescent device of claim 1, wherein the dielectric layer comprises a high-resistivity material having an electrical resistivity no less than about $10^8$ ohm-cm.

24. The electroluminescent device of claim 23, wherein the high-resistivity material is selected from the group consisting of silicon nitride, boron nitride, aluminum nitride, silicon oxide, aluminum oxide, paralene, polyimide and polyvinylidene fluoride.

25. The electroluminescent device of claim 1, wherein the cavity is axially symmetric.

26. The electroluminescent device of claim 25, wherein the cavity has a constant cross-sectional area along the cavity axis.

27. The electroluminescent device of claim 25, wherein the cavity has a smaller cross-sectional area at the dielectric layer than at least one of the electron-injection or hole-injection electrode layers.

28. The electroluminescent device of claim 1, further comprising:

an additional hole-injection electrode layer for injecting holes into the electroluminescent material; and an additional dielectric layer interposed between the electron-injection electrode layer and the additional hole-injection electrode layer, wherein the cavity extends through at least one hole-injection electrode layer, the electron-injection electrode layer and each dielectric layer, and further wherein the electroluminescent material is in electrical contact with each electrode.

29. The electroluminescent device of claim 1, further comprising:

an additional electron-injection electrode layer for injecting electrons into the electroluminescent material; and an additional dielectric layer interposed between the hole-injection electrode layer and the additional electron-injection electrode layer, wherein the cavity extends through at least one electron-injection electrode layer, the hole-injection electrode layer and each dielectric layer, and further wherein the electroluminescent material is in electrical contact with each electrode.

30. The electroluminescent device of claim 1, wherein the electroluminescent material emits photons when an operating voltage is applied between the hole-injection and the electron-injection electrode layers, and further wherein the dielectric layer has sufficient thickness and dielectric strength to withstand at least about 2 volts over the operating voltage.

31. A method for forming an electroluminescent device comprising the steps of:

(a) providing a layered structure comprising
   a hole-injection electrode layer,
   an electron-injection electrode layer,
   a dielectric layer interposed between the hole-injecting and electron-injecting electrode layers, and
   a cavity extending through at least the dielectric layer and one of the electrode layers, the cavity having an interior cavity surface comprising a hole-injection electrode region, an electron-injection electrode region and a dielectric region; and (b) coating the interior cavity surface with an electroluminescent material such that the electroluminescent material is in electrical contact with the hole-injection and electron-injection electrode regions of the interior cavity surface.

32. The method of claim 31, wherein step (a) comprises:

(a1) providing a preform layered structure comprising the hole-injection electrode layer, the electron-injection electrode layer and the dielectric layer interposed between the hole-injecting and electron-injecting electrode layers, and (a2) etching through at least a portion of the preform layered structure with an etchant to form the cavity having the interior cavity surface.

33. The method of claim 32, wherein the etchant comprises an isotropic etchant.

34. The method of claim 32, wherein the etchant comprises an anisotropic etchant.

35. The method of claim 32, wherein step (a1) comprises forming the dielectric layer on either the hole-injection or the electron-injection electrode layer through chemical vapor deposition.

36. The method of claim 31, wherein step (a) comprises:

(a1) forming the layered structure around a sacrificial member having a desired shape for the cavity, the layered structure comprising the hole-injection electrode layer, the electron-injection electrode layer, and the dielectric layer interposed between the hole-injecting and electron-injecting electrode layers, wherein the sacrificial member extends through the dielectric layer and at least one of the hole-injection or electron electrode layers; and (a2) removing the sacrificial member from the layered structure to form the cavity, thereby exposing the interior cavity surface.

37. The method of claim 31, further comprising, between steps (a) and (b), step (c) modifying the interior cavity surface.

38. The method of claim 37, wherein step (c) comprises attaching a surface-altering moiety to the interior cavity surface.

39. The method of claim 31, further comprising (c) subjecting the electroluminescent material to a reduced pressure.

40. The method of claim 31, further comprising (c) subjecting the electroluminescent material to heat.

41. The method of claim 31, wherein step (b) comprises printing the electroluminescent material into the cavity.

42. An electroluminescent display device comprising a layered structure of:

a hole-injection electrode layer, an electron-injection electrode layer, and a dielectric layer interposed between the hole-injection and electron-injection electrode layers;

a plurality of cavities each extending through a portion of the layered structure such that each cavity has an interior cavity surface comprising a hole-injection electrode region, an electron-injection electrode region and a dielectric region; and an electroluminescent material in electrical contact with the hole-injection and electron-injection electrode regions of each interior cavity surface.

43. The electroluminescent display device of claim 42, wherein the plurality of cavities is arranged in an array.

44. The electroluminescent display device of claim 43, further comprising an emission modifier in at least one cavity.

45. The electroluminescent display device of claim 43, wherein each cavity has a diameter of about 1 to 12 micrometers.

* * * * *

UNITED STATES PATENT AND TRADEMARK OFFICE
CERTIFICATE OF CORRECTION

PATENT NO.   : 6,593,687 B1
DATED        : July 15, 2003
INVENTOR(S)  : Qibing Pei et al.

It is certified that error appears in the above-identified patent and that said Letters Patent is hereby corrected as shown below:

Column 1,
Line 5, after "CROSS-REFERENCE TO RELATED APPLICATIONS" and before the section entitled "TECHNICAL FIELD," please insert the following section:

-- REFERENCE TO GOVERNMENT SUPPORT
This invention was funded in part by the United States Office of Naval Research under Contract No. N00014-99-C-0274. The United States Government has certain rights in this invention. --

Signed and Sealed this

Sixteenth Day of September, 2003

JAMES E. ROGAN
*Director of the United States Patent and Trademark Office*